(12) United States Patent
Toriser (10) Patent No.: US 8,608,787 B2
(45) Date of Patent: Dec. 17, 2013

(54) DEVICE AND METHOD FOR IRRADIATING TISSUE WITH LIGHT PULSES

(75) Inventor: Walter Toriser, Vienna (AT)

(73) Assignee: Technische Universitat Wien, Vienna (AT)

( * ) Notice: Subject to any disclaimer, the term of this patent is extended or adjusted under 35 U.S.C. 154(b) by 804 days.

(21) Appl. No.: 12/663,244

(22) PCT Filed: Jun. 11, 2008

(86) PCT No.: PCT/AT2008/000203
§ 371 (c)(1),
(2), (4) Date: Dec. 4, 2009

(87) PCT Pub. No.: WO2008/151340
PCT Pub. Date: Dec. 18, 2008

(65) Prior Publication Data
US 2010/0168824 A1    Jul. 1, 2010

(30) Foreign Application Priority Data

Jun. 11, 2007   (AT) .................................. A 905/2007

(51) Int. Cl.
*A61N 5/06* (2006.01)

(52) U.S. Cl.
USPC ............................................ 607/90; 607/88

(58) Field of Classification Search
USPC .................................................... 607/88, 90
See application file for complete search history.

(56) References Cited

U.S. PATENT DOCUMENTS

| | | | |
|---|---|---|---|
| 4,930,504 A * | 6/1990 | Diamantopoulos et al. | 607/88 |
| 5,259,380 A | 11/1993 | Mendes et al. | 607/115 |
| 5,698,866 A | 12/1997 | Doiron et al. | 257/99 |
| 6,221,095 B1 | 4/2001 | Van Zuylen et al. | 607/88 |
| 6,736,807 B2 * | 5/2004 | Yamazaki et al. | 606/9 |
| 2005/0055070 A1 * | 3/2005 | Jones et al. | 607/88 |
| 2006/0084097 A1 | 4/2006 | Hu et al. | 435/6 |
| 2007/0038206 A1 * | 2/2007 | Altshuler et al. | 606/20 |

FOREIGN PATENT DOCUMENTS

| | | |
|---|---|---|
| DE | 101 28 629 | 12/2002 |
| WO | WO 97/35635 | 10/1997 |
| WO | WO 98/50034 | 11/1998 |
| WO | WO 02/062420 | 8/2002 |
| WO | WO 2006/005088 | 1/2006 |

OTHER PUBLICATIONS

Miller et al., "A study of the photodegradation of leukotriene $B_4$ by ultraviolet irradiation (UVB, UVA)," *British Journal of Dermatology*, 120:145-152, 1989.

* cited by examiner

*Primary Examiner* — Armando Rodriguez
(74) *Attorney, Agent, or Firm* — Fulbright & Jaworski LLP (57) ABSTRACT

The invention relates to a device (1) for irradiating tissue (G) with light pulses (L), comprising a housing (2), at least one light source (3) for emitting the light pulses (L) with a wavelength (λ) of from 600 nm to 660 run, a modulator (4) and a power stage (6) for generating the light pulses (L), and with an activating element (5). For creating a device (1) which is as small, as cost-efficient and as effective as possible, by which as good a therapy success as possible is achieved in various applications, the modulator (4) is designed for generating the light pulses (L) with a pulse frequency (f) of from 1 to 10 Hz, and the power stage (6) is designed for emitting the light pulses (L) with an energy which causes breaking up of the photosensitizer in the photodynamic therapy and evokes a frequency doubling or a two-photon absorption (TPA) in the tissue (G) when treating inflammations without a sensitizer.

39 Claims, 5 Drawing Sheets

DEVICE AND METHOD FOR IRRADIATING TISSUE WITH LIGHT PULSES

This application is a national phase application under 35 U.S.C. §371 of International Application No. PCT/AT2008/000203 filed 11 Jun. 2008, which claims priority to Austrian Application No. A 905/2007 filed 11 Jun. 2007. The entire text of each of the above-referenced disclosures is specifically incorporated herein by reference without disclaimer.

The invention relates to a device for irradiating tissue with light pulses, comprising a housing, at least one light source for emitting the light pulses with wavelengths of from 600 nm to 660 nm, a modulator and a power stage for generating the light pulses, and with an activating element.

Furthermore, the present invention relates to a method for irradiating tissue with light pulses emitted by light sources and having wavelengths of between 600 nm and 660 nm.

In principle, the present invention is directed to the irradiation of human tissue, in particular of the skin and of the regions located therebelow. However, also applications are possible in which, e.g. via an endoscope or the like, the tissues of inner organs are irradiated with light and diseases are treated accordingly. Basically, also an application on animals is possible.

Devices and methods for irradiating tissue with light for different purposes are known. By means of phototherapeutic methods, certain skin diseases can be alleviated or cured using an irradiation with light of a special wavelength or with combinations of various wavelengths. For instance, skin diseases, such as, e.g., psoriasis, can be treated by irradiation with ultraviolet light. The photodynamic therapy (PDT) refers to a method for treating tumours and other changes of tissue with light in combination with a light-sensitive substance, a so-called photosensitizer. The photosensitizer administered to the patient is selectively enriched in the tumour. By irradiating with light of a suitable wavelength, toxic substances are produced by photophysical processes, which substances specifically damage the tumour. What is detrimental in this case are the side effects of the photosensitizer.

WO 2006/005088 A1, e.g., describes a device for the photodynamic treatment of diseases of the tissue by using a power light-emitting diode in the red light spectrum, and the effect of the irradiation on the patient is detected by means of a sensor. Thereby lower power densities can be used and the thermal load on the patient can be reduced. However, comparatively large cooling elements are required for conducting away the relatively high thermal dissipation losses which, nevertheless, do occur.

U.S. Pat. No. 5,698,866 A shows a device for photodynamic therapy with an array of light-emitting diodes, which allows for a precise regulation of the exposure to light and a precise dosimetry using a sensor formed by a fibre-optic system.

WO 02/062420 A1 also shows a device for the photodynamic therapy, in which sensors are provided which are employed for controlling the duration of irradiation. The device has a comparatively complex and large construction and, therefore, is only suitable to be used in hospitals or doctor's offices.

WO 97/35635 A2 describes an apparatus for the treatment of biological tissue by means of laser light with preferred wavelengths of 1064 nm and 2500 nm. What is detrimental is that the degree of absorption of a biological tissue at such wavelengths is relatively low and, thus, very high power densities must be used for achieving an effect, which power densities in turn are painful for the patient.

In all the photodynamic therapy methods, the photosensitizer in most instances has undesired side effects and negative impacts.

U.S. Pat. No. 6,736,807 B2 shows a depilating device with the use of laser light. For a lasting destruction of the roots of the hair, comparatively high power densities must be used. The wavelengths used do not penetrate very far into the tissue to be treated, and therefore a treatment of deeper tissue regions is not possible with such laser light sources.

Moreover, methods and devices for stimulating acupuncture points by means of laser light are known. DE 101 28 629 A1, e.g., describes a light-emitting device designed as a skin patch, in which light pulses generated by a laser diode are used for the acupuncture treatment instead of the pricks generated by acupuncture needles.

The present invention has as its object to provide a device for irradiating tissue with light, which device is to be as small, as cost-efficient and as effective as possible, as well as a method which results in as great a therapy success as possible with as short a duration of treatment and as little pain as possible for the patient and which, moreover, lends itself to different therapy applications. In particular, the present device and the present method shall be suitable for treating inflammatory tissue diseases and entail as slight burdens and side-effects for the patient as possible. Yet, the device shall also be suitable for a use by the patient at home and, accordingly, should be as handy, as simple and as safe to be operated as possible. Disadvantages of the prior art shall be avoided or, at least, reduced.

The object according to the invention is achieved by an above-indicated device for irradiating tissue, wherein the modulator is designed for generating the light pulses with a pulse frequency of from 1 to 10 Hz and the power stage for generating the light pulses is designed with an energy which causes a two-photon absorption or a frequency doubling in the irradiated tissue when treating inflammations without sensitization, or which causes a breaking up of a photosensitizer in the photodynamic therapy, respectively. The present device for irradiating tissue with light pulses is excellently suitable for treating a number of skin and tissue diseases, respectively, in particular inflammatory diseases, such as, e.g., psoriasis, neurodermatitis, mycoses, or also for the treatment of melanomas, the latter with the addition of suitable photosensitizers. By pulsing the light with 1 to 10 Hz, any pain can be clearly reduced at still relatively high power densities as compared to conventional irradiation devices. The reason for the selection of the pulse frequency resides in the effect of that time which is required in order to transport away destroyed cells or cell parts via the blood. Tests have, e.g., shown that at least 0.2 seconds are required for those parts which have been destroyed by the light to be transported away via the blood. In case of a higher pulse frequency, or in case of a lower pulse frequency, respectively, it would not be possible for the material to be transported away to be removed by the blood in time before the next light pulse, manifesting itself as a reduced depth of penetration and as pain. Moreover, due to the pulsing of light, the heat development is reduced and, thus, also the pain sensation due to the influence of heat is impossible. Apart from the pulse frequency used, also the energy of the light pulses is essential which, according to the invention, is chosen such that a so-called two-photon absorption or a doubling of frequency will occur within the tissue. At two-photon absorption (TPA), two photons are at the same time absorbed by an atom or molecule in the irradiated tissue and, at the same time, the atom or molecule is thereby converted into an excited state. Due to non-linear processes, a doubling of the frequency, or a halving of the wavelength of the irradiating light occurs, which, in the instant case, causes the generation of a radiation in the UVB range (i.e. at a wavelength λ in the range of from 300 nm to 330 nm). The UVB radiation may cause a destruction of substances that are responsible for the disease of the tissue. In the literature, particularly leukotriene $B_4$ (LTB4) or its derivatives, that is a hormone-like substance occurring in connection with allergic and inflammatory reactions of the body, are mentioned (B. Millar et al.: A study of the photodegradation of leukotriene $B_4$ by ultraviolet irradiation (UVB, UVA), British Journal of Dermatology (1989) 120, pp. 145-152). By the two-photon absorption or frequency doubling, the active substance leukotriene $B_4$ (LTB4) or its derivatives can be inhibited or converted and, thus, the disease can be treated and/or cured, respectively. For the occurrence of the two-photon absorption or frequency doubling within the tissue, comparatively high power densities are required which must be adapted to the respective application. Tests have shown that two-photon absorption or frequency doubling are measurable within the tissue. Thus, for treating certain diseases, the light dose required can be determined from experience and, subsequently, depending on the pulse frequency used and the pulse duty factor used, the power density of the light sources required for two-photon absorption can be determined. Compared to known devices, it is possible with the subject irradiation device to obtain an optimum treatment result by, e.g., direct UVB irradiation or by photosensitizers within a very short duration of treatment and without any pain for the patient and, as a rule, without any side effects. By using red light in the wavelength range indicated it is, therefore, possible to attain an optimum absorption of the light radiation within the tissue, wherein at the site of the disease, i.e. within the tissue, UVB radiation is generated which leads to the inhibition or destruction of the mediators responsible for the disease. If the tissue were directly irradiated with light in the UVB range, the penetration depth would be very low, since tissue consists mainly of water which is not transparent for the UVB radiation. In order to achieve an effect within the tissue nonetheless, the power densities of the light sources therefore would have to be chosen appropriately high which, in turn, would cause pain on account of the heat occurring. Moreover, the direct irradiation with UVB light would have further disadvantages due to the risk of cancer.

According to a further feature of the invention it is provided for the modulator for generating the light pulses to be designed with a pulse duty factor of ≤0.6. Tests have shown that an upper limit of 60% is the best for the pulse duty factor. Theoretically, the lower limit can be chosen deliberately, yet nevertheless it is defined by the fact that the treatment time should remain within reasonable limits. If the pulse duty factor were chosen very small, the treatment time for transmitting the dose of light required for the disease to be treated would have to be chosen to be correspondingly long. Short treatment times are, of course, advantageous for the patient, wherein e.g. 30 to 60 minutes can be indicated as the upper tolerance limit.

The power stage for generating the light pulses preferably is designed with a peak power density of ≥50 mW/cm², based on the pulse duty factor ΔT/T. At these values, optimum results could be achieved.

According to a further feature of the invention it is provided that the at least one light source is fastened to the housing such that the at least one light source can be directly arranged on the surface of the tissue to be irradiated. By such a design of the irradiation device, deeper regions of the tissue can be treated with light. For instance, joints can be irradiated with light for treating inflammatory arthropathies.

If several light sources are arranged along a line, regions, such as, e.g., joint spaces, yet also the tissue between the ribs, can be treated specifically. As required, the light sources can be arranged in different patterns.

As an alternative to the above-mentioned embodiment, also spacer elements can be provided for creating a defined distance of the at least one light source from the surface of the tissue to be treated. This embodiment is particularly suitable for irradiating the skin and tissue regions in the immediate vicinity of the skin surface. The space between the light sources and the surface of the tissue to be treated is adjusted accordingly to the disease to be treated, on the one hand, and also to the light sources used, on the other hand.

In order to be able to use the device also for different applications, it is also possible to design the spacer elements adjustable. Various constructions can be employed for providing the adjustability. Moreover, by changing the distance between light sources and the skin surface, the energy density can be changed, with a simultaneous change of the area being irradiated.

With the embodiment of the device in which the light sources are arranged at a distance from the surface of the tissue to be treated, it may be advantageous to arrange a lens for bundling the light rays in front of the at least one light source, or to integrate the lens in the light source, e.g. in the light-emitting diode.

If there are several light sources, the latter are arranged in the ray direction preferably at an inclination relative to one another, so that all the light rays are directed at the desired region to be treated. Due to the bundling of the light rays, the power density of the light sources can be reduced to a necessary minimum and, thus, also the power loss of the light sources manifested as a heat development can be reduced. The result is a handy construction of the device which allows for wide applications also by the patients themselves, due to which frequent trips to the hospital or to the doctor can be omitted.

If according to a further feature of the invention, a sensor is provided for detecting the light rays reflected from the surface of the irradiated tissue, the amount of light absorbed by the tissue can, on the one hand, be estimated and used, e.g., for controlling the irradiation device, or also the success of the therapy can be quantified and the duration of treatment can be fixed. On account of the irradiation, usually the composition of the tissue changes, expressing itself in a changed absorption ability of the tissue. Thus, via the intensity of the reflected light, the quality of the treatment can be judged and the optimum duration of treatment can be fixed.

Advantageously, the sensor is formed by an optical fiber and a photosensitive element, the free end of the optical fiber being arranged at a defined distance from the surface of the tissue, and the other end of the optical fiber being connected to the photosensitive element. The light reflected by the tissue is conducted through the optical fiber to the photosensitive element. For detecting the reflected light, merely the particularly thin optical fiber is necessary which hardly influences the light rays of the light source.

Advantageously, the distance of the free end of the optical fiber is changeable so as to provide for a calibration and adaptation of the measurement of the radiation reflected by the skin surface.

Furthermore, a separate reference light source and a sensor for detecting the reference light radiation reflected by the tissue can be provided.

In doing so, the wavelength of the reference light source is optimally adjusted to the respective fields of use. In this respect, the use of UVB radiation having a wavelength of between 280 nm and 320 nm for determining the success of treatment has been particularly suitable. The power density of the reference light source is particularly low compared to the power density of the light sources, so that the UVB irradiation cannot exert any damaging effect on the tissue. Via the measurement of the absorption ability of UV radiation by the tissue being treated, the success of the treatment can be detected and quantified, respectively, in a suitable manner.

If the sensor is connected to an evaluation unit, the measured, reflected light can be evaluated accordingly and, e.g., quantified.

If the evaluation unit is connected to the modulator for generating the light pulses, a closed control circuit can be formed, wherein parameters of the light pulses, such as power density, pulse frequency, pulse duty factor, pulse duration or the like can be regulated as a function of the measured, reflected light.

Advantageously, the modulator for generating the light pulses is designed with a pulse frequency of 2.5 Hz and with a pulse duty factor of 0.5. As already mentioned above, with a photodynamic therapy, approximately 0.2 seconds are required for removing the cell components destroyed during the irradiation via the bloodstream. With the parameters indicated, the pulse duration will exactly correspond to these 0.2 seconds.

Since the subject device shall also be suitable to be used by the patients themselves, it is advantageous if there are no or no substantial adjustment possibilities and if the required parameters are definitely and non-changeably pre-adjusted. It may, however, be advantageous for a memory to be provided for storing various values for the pulse frequency, the pulse duty factor and the power density as well as an operating element for selecting the desired values from the memory. In this way, various adjusted positions can be stored in the device, from which the operator of the device chooses the desired combination with the help of the operating element without the risk of maladjustments and, thus, a false treatment.

Advantageously, at least one light source is formed by at least one light-emitting diode. The light-emitting diode can have an integrated lens or it may also be used without a lens. At present, light-emitting diodes in the wavelength range indicated, in particular in the range of between 637 nm and 643 nm, can be obtained at particularly reasonable prices.

If batteries are provided for the voltage supply, the device can be used independently of an external voltage supply. It is then advantageous to use rechargeable batteries so as to make it possible to use the device often without having to change the batteries.

In order to prevent a damage to the eyes of a person by the relatively intensive red light radiation of the lightsources, a means for detecting a contact of the light sources or of a spacer element with the surface of the tissue to be irradiated may be provided. By such a detection means which may, e.g., be formed by a microswitch or by an optical element, an activation of the light sources will become possible only if the device is applied at the desired tissue region.

For this purpose, the detection means preferably is connected to the modulator so that an activation of the modulator is allowable only if a contact of the light sources or of a spacer element with the surface of the tissue to be irradiated has been recognized.

Even though the device is to be constructed as simple and robust as possible, a display for displaying the operating state or certain parameters may be provided. The display may be formed in the simplest manner by one or more light-emitting diodes or by a seven segment display up to an LCD display.

Advantageously, the housing is designed to be splash-proof so that the components contained therein are appropriately protected.

To protect the light sources and the power stage from over-heating, they may be connected to an appropriately dimensioned cooling element. For an optimum heat transport, also appropriate thermally conductive materials, such as, e.g., thermally conductive paste, may be used.

The object according to the invention is also achieved by an above-indicated method for irradiating tissues with light pulses, wherein the light pulses are emitted with a pulse frequency of from 1 to 10 Hz, and the energy of the light radiation is adjusted for evoking a two-photon absorption or frequency doubling in the irradiated tissue. As regards the advantages attainable thereby and the further method characteristics according to the invention, reference is made to the above description of the device and the appended drawings and their description.

Accordingly, the present invention will be explained in more detail by way of the accompanying drawings.

Therein.

Figure 1:
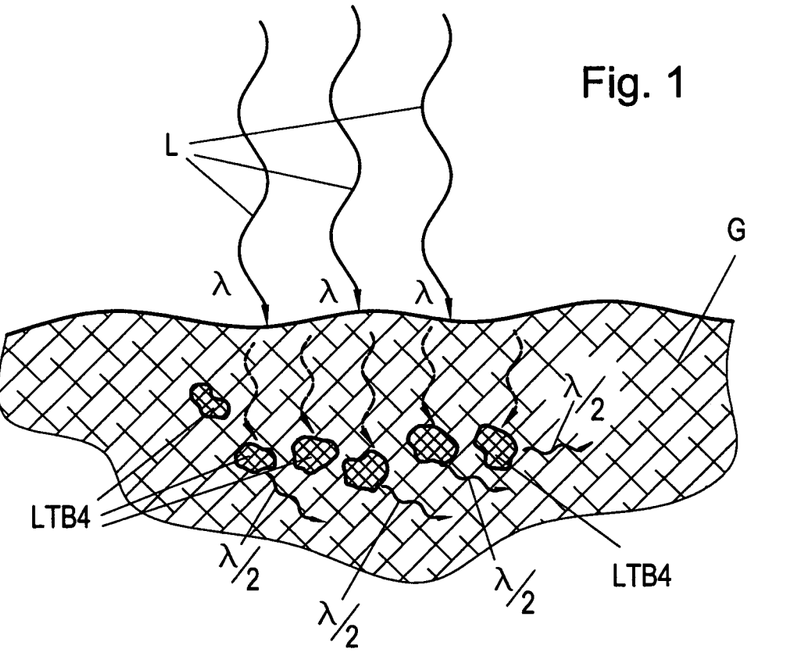
FIG. 1 shows a schematic illustration elucidating the two-photon absorption or frequency doubling within the tissue.

FIG. 1 shows a scheme for elucidating the two-photon absorption (TPA) or frequency doubling occurring in tissue G. Tissue G is irradiated with light pulses L of the wavelength $\lambda$ of between 600 nm and 660 nm. Red light of this wavelength $\lambda$ is in the so-called water window and, therefore, is particularly suitable, since at this wavelength $\lambda$ human or animal tissues are particularly transparent due to their high water content and, thus, very much light energy can be absorbed by the photosensitizer in tissue G. In the inflamed tissue (not in tumours), there are so-called leukotrienes which increasedly occur in allergic and inflammatory reactions. In particular, leukotriene $B_4$ (LTB4) or its derivatives are being mentioned in the context of inflammatory diseases of the tissue G. If the effect of the leukotriene $B_4$ (LTB4) or its derivatives is inhibited, the disease can be alleviated or cured. By an appropriate energy of the light pulses L, due to a frequency doubling or two-photon absorption (TPA), a frequency doubling or wavelength halving occurs in the leukotriene $B_4$ (LTB4) and/or its derivatives, which finally leads to an inhibition and/or destruction of the leukotriene $B_4$ (LTB4) or its derivatives. What is responsible for this in any event is a non-linear effect, in which a doubling of the frequency of the irradiating light pulses L occurs. This is indicated in FIG. 1 by light waves in tissue G by the wavelength $\lambda/2$, i.e. in the range between 300 nm and 330 nm, i.e. in the UVB range. Tissue G, thus, is irradiated with red light having a wavelength $\lambda$ of from 600 nm to 660 nm, and the leukotriene $B_4$ (LTB4) is inhibited or converted by the frequency doubling or two-photon absorption (TPA) occurring.

Figure 2:
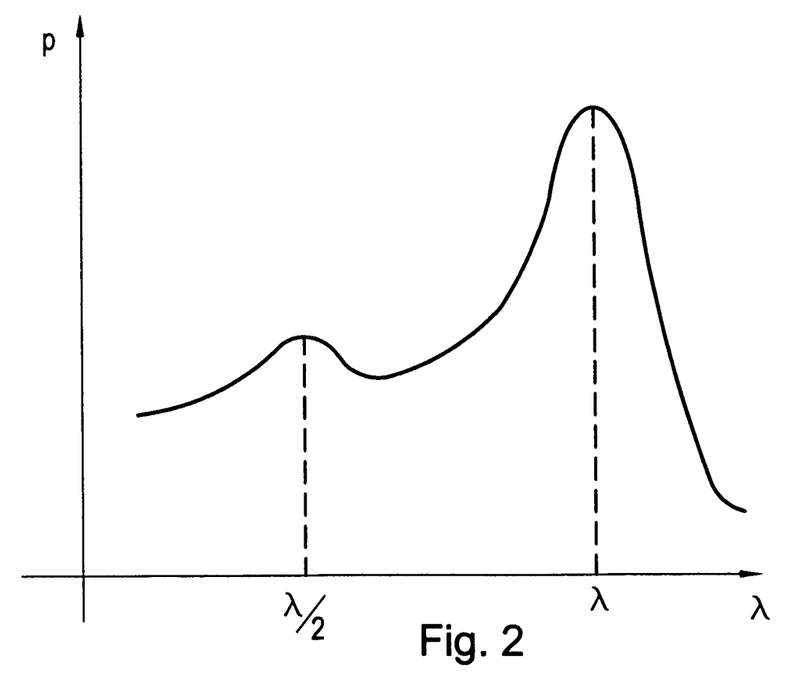
FIG. 2 shows the spectrum of the light intensity occurring within the tissue.

As can be seen in the spectrum according to FIG. 2, a certain power density p of the measured light could be recorded at half the wave length λ/2 of the irradiating light pulses L by means of measurement technique, which is not the second harmonic of the light radiation of the light source.

Figure 3:
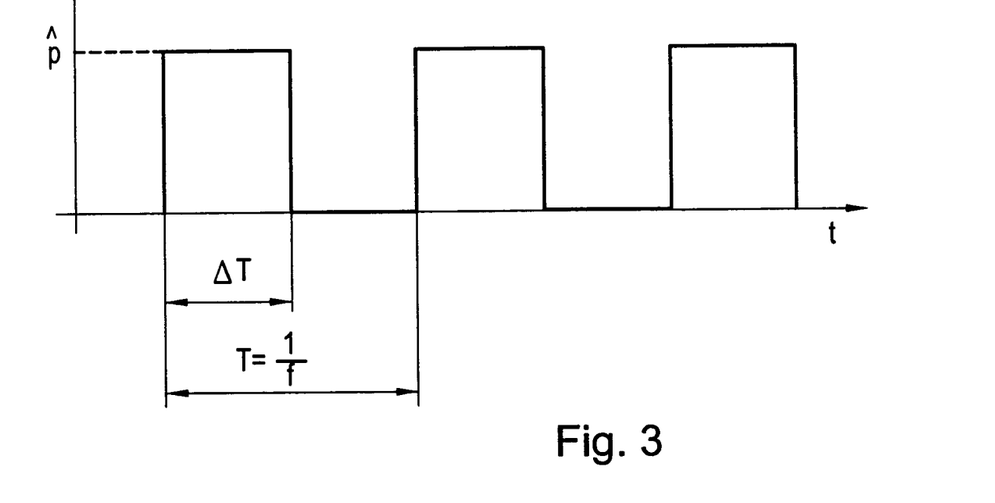
FIG. 3 shows the light pulses as a function of time.

FIG. 3 shows the essential parameters of the light pulses L as a function of time t. Accordingly, the light pulses L are repeated with a pulse frequency f, or a period duration T=1/f, and a pulse duty factor ΔT/T of ≤0.6, or 60%, respectively, is selected. The peak power density p̂ preferably is ≥0.05 Watt/cm², based on the pulse duty factor ΔT/T.

Figure 4:
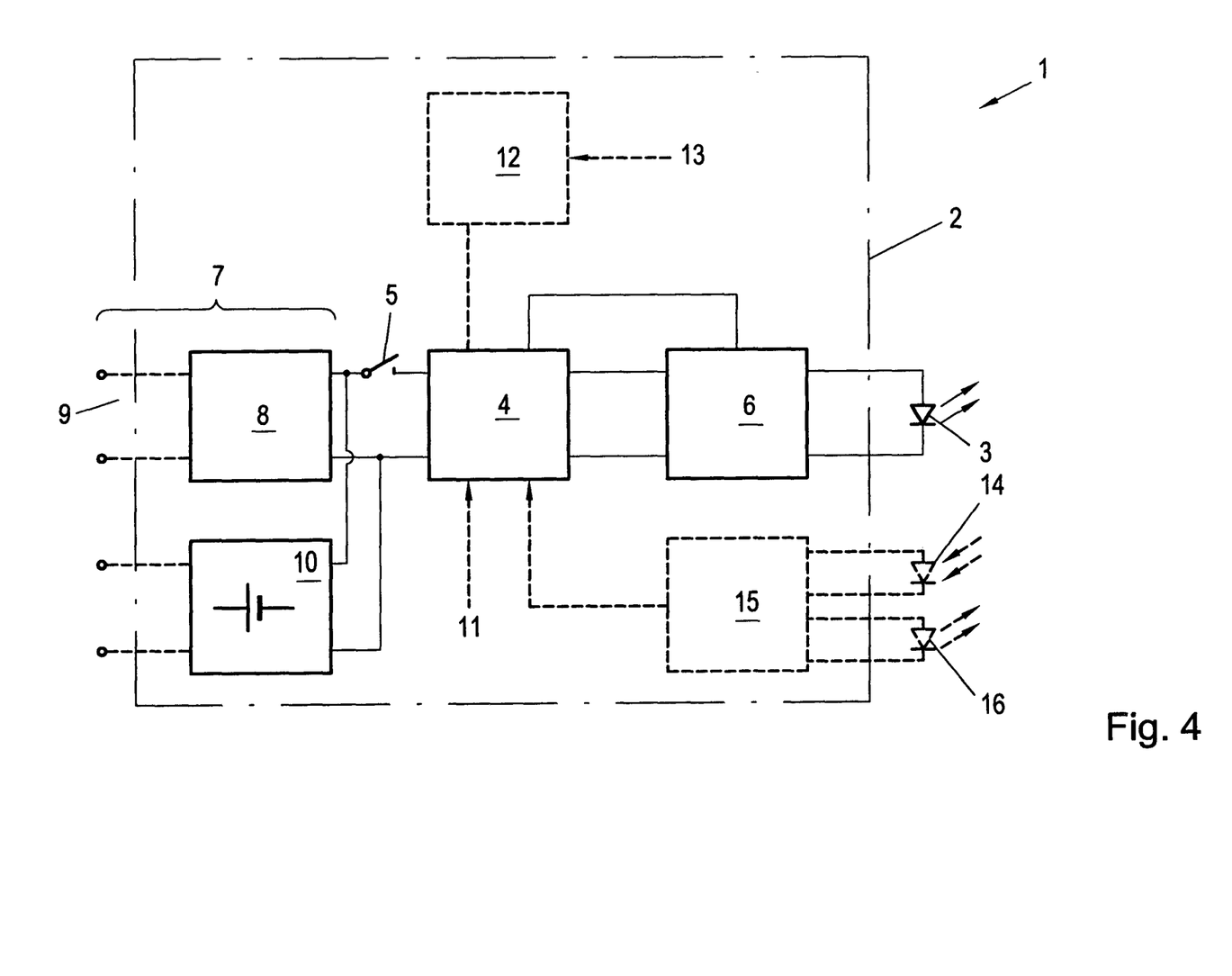
FIG. 4 shows a block diagram of an embodiment of a device according to the invention for irradiating a tissue with light pulses.

FIG. 4 shows a block diagram of an embodiment of the device 1 according to the invention for irradiating tissue G with light pulses L, comprising a housing 2 with at least one light source 3 for emitting light pulses L with a wavelength λ of from 600 nm to 660 nm, a modulator 4 for generating the light pulses L, and an activating element 5 for activating the irradiation device 1. The modulator 4 activates a power stage 6 with the desired pulse frequency f and the respective pulse duty factor ΔT/T, so that the light sources 3 will be supplied with a corresponding current. The light sources 3 preferably are light-emitting diodes which can be purchased at particularly reasonable prices and in small designs.

To supply the components of the device 1 with electric energy, a voltage supply 7 is provided which may be formed by a power adapter 8 and terminals 9 for connection to a power outlet or by a—preferably rechargeable—battery 10. Via a setting member 11, parameters of the light pulses L, such as, e.g., pulse frequency f, pulse duty factor ΔT/T or the peak power density p̂ can be changed. However, an embodiment of the device 1, in which as far as possible the parameters cannot be changed by the patients, is preferred. In this way, a false operation and, thus, a false treatment with the device 1 is prevented. However, a memory 12 may be provided in which different values for the pulse frequency f, the pulse duty factor ΔT/T and the peak power density p̂ can be stored, which can be called up and adjusted via an operating element 13. For instance, different parameters can be stored in memory 12 for treating different diseases.

Via a sensor 14, the light irradiation reflected by tissue G may be detected and supplied to an evaluation unit 15, e.g., so as to be able to quantify the light irradiation absorbed by tissue G and the success of the therapy. If the evaluation unit 15 is connected to the modulator, a regulation of the parameters of the light pulses L can be carried out due to the reflected light irradiation measured. A reference light source 16 may be provided to which the sensor 14 is adapted with regard to the wavelength λ. In this case, a wavelength λ in the UV-range is particularly suitable, since the absorption ability of the tissue in the UV range is changed in dependence on the treatment and, thus, from the reflected light irradiation conclusions can be drawn regarding the success of the treatment.

The device 1 according to the invention may be of a particularly small design so that an ambulant use or a use by the patients at their homes is possible. Of course, the size of the irradiation device 1 will be adapted to the size of the tissue area to be treated. For the treatment of larger body regions it is, of course, also possible to use floor-mounted appliances.

Figure 5A:
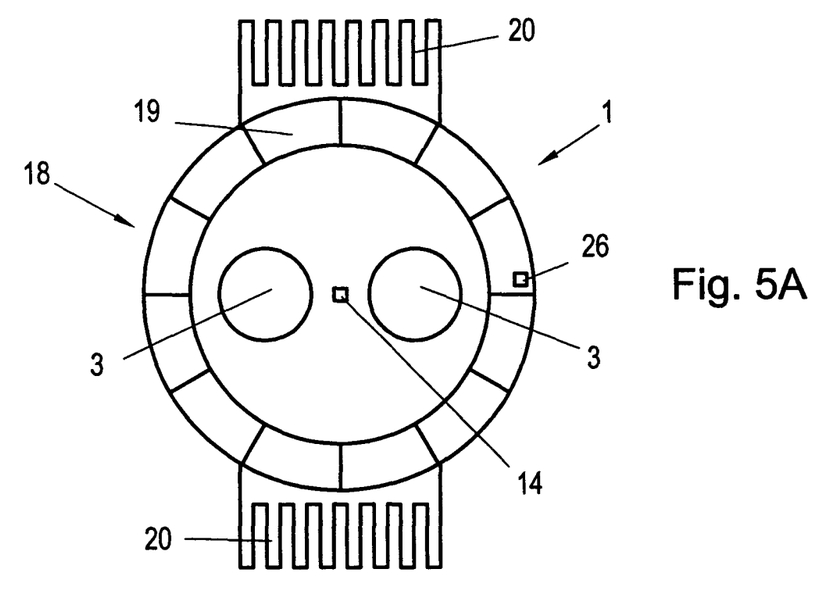
FIGS. 5A and 5B show two views of an embodiment of an irradiation device.
Figure 5B:
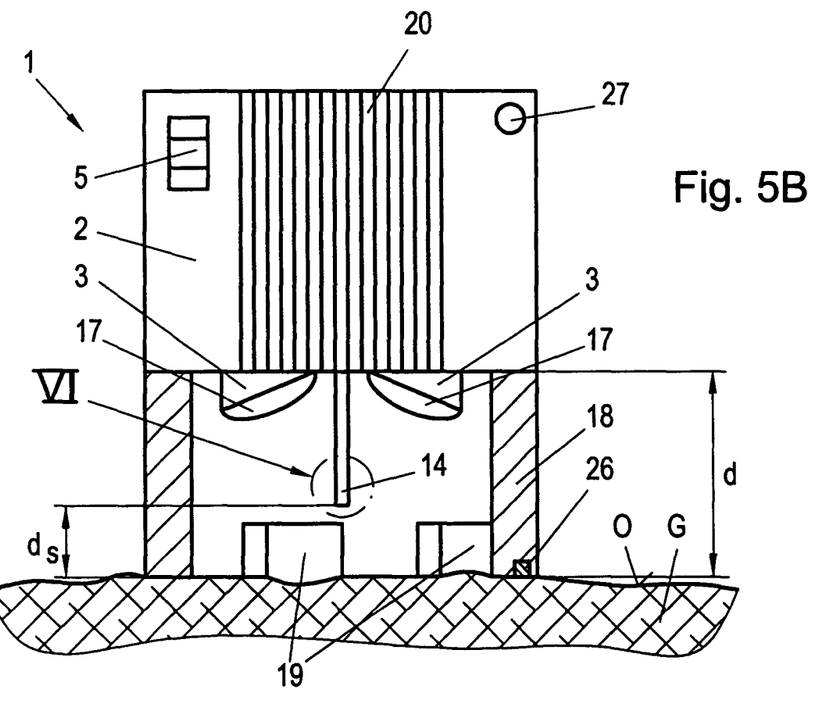

FIGS. 5A and 5B show various views of an embodiment of the irradiation device 1, wherein two light sources 3 are arranged at a defined distance d from the surface O of the tissue G to be treated. For bundling the light rays, lenses 17 are arranged in front of the light sources 3 and, moreover, the two light sources 3 are arranged to be inclined towards each other in the direction of the rays. The distance d of the light sources 3 to the surface O of the tissue G to be treated is defined by a spacer element 18 which, in the example illustrated, is realized by a cylindrical element having appropriate recesses 19 at its side facing the tissue G. By means of the recesses 19, an air supply is ensured and overheating of the tissue G under the device 1 is prevented. The spacer elements 18 may also be designed to be adjustable so as to achieve an adjustment of the distance d of the light sources 3 to the surface O of the tissue G to be treated (not illustrated). This adjustability of the spacer elements 18 may, e.g., be realized by a screw thread or by other constructions.

The most important components of the device 1 are arranged within a—preferably splash-proof—housing 2, at which cooling elements 20 may be arranged for conducting away the thermal dissipation loss. In particular, the cooling elements 20 are in thermal contact with the light sources 3 and the power stage 6. Via an activation element 5, the device 1 is switched on and off.

Figure 6:
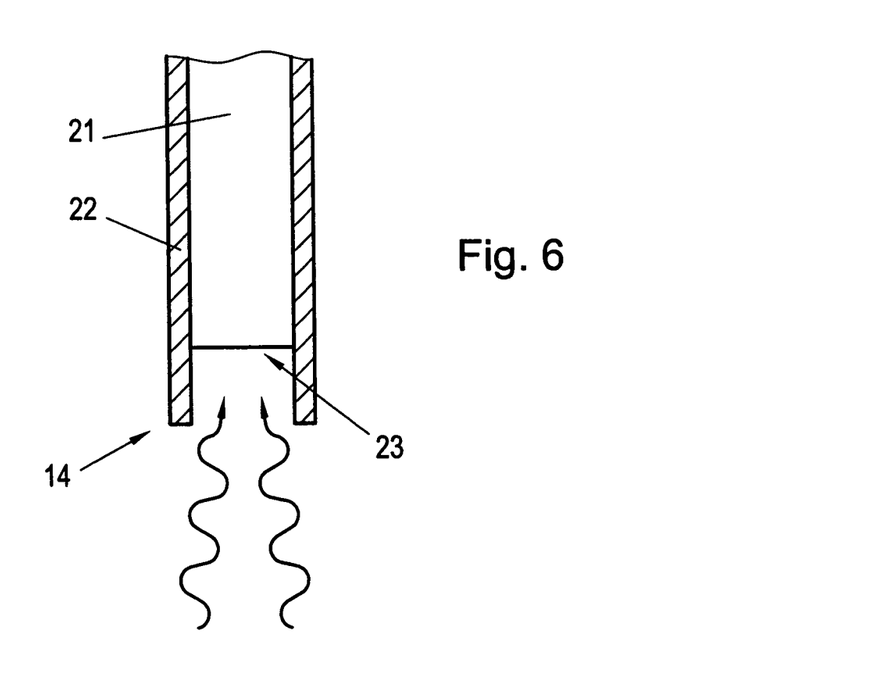
FIG. 6 shows detail VI of FIG. 5B in an enlarged illustration.

Via a sensor 14, the light radiation reflected by the tissue G can be recorded and evaluated. As illustrated in FIG. 6 on an enlarged scale, the sensor 14 is, e.g., formed by an optical fiber 21 having an insulation 22 which, preferably, projects somewhat beyond the free end 23 of the optical fiber 21 so that only the light reflected by the tissue G is detected. The other end of the optical fiber 21 (not illustrated) is connected to a suitable photosensitive element within the housing 2, and the incoming light radiation is appropriately evaluated. In order to enable an adaptation and calibration of the device, the distance $d_S$ of the sensor 14 from the surface O of the tissue G may be changeable. In the arrangement of two light sources 3 illustrated, the sensor 14 preferably is located between the light sources 3 at the centre of the cone of light obtained.

Furthermore, a means 26 may be provided for detecting a contact of the light sources 3 or of the spacer element 18 with the surface O of the tissue G to be irradiated, so as to allow for an activation of the light sources 3 only with the device 1 applied and to prevent damage to the eyes of the patient or of other persons by the intensive red light radiation of the light sources 3. The detection means 26 may, e.g., be formed by a microswitch or by a photosensitive element that is connected to a part of the electronic circuit of the device 1.

Finally, a display 27 may be provided, which displays the operating state of the batteries 10 or the like. Instead of a display 27 formed by a light-emitting diode or the like, also an LCD-display may be provided which may provide the user of the device 1 with more information.

Figure 7A:
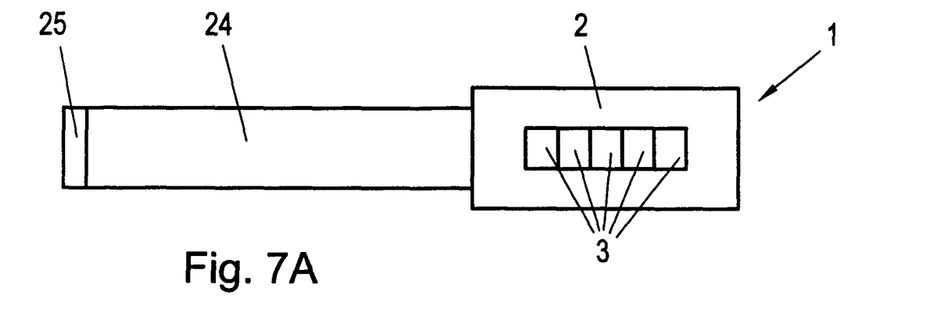
FIGS. 7A and 7B show two views of a further embodiment of an irradiation device.
Figure 7B:
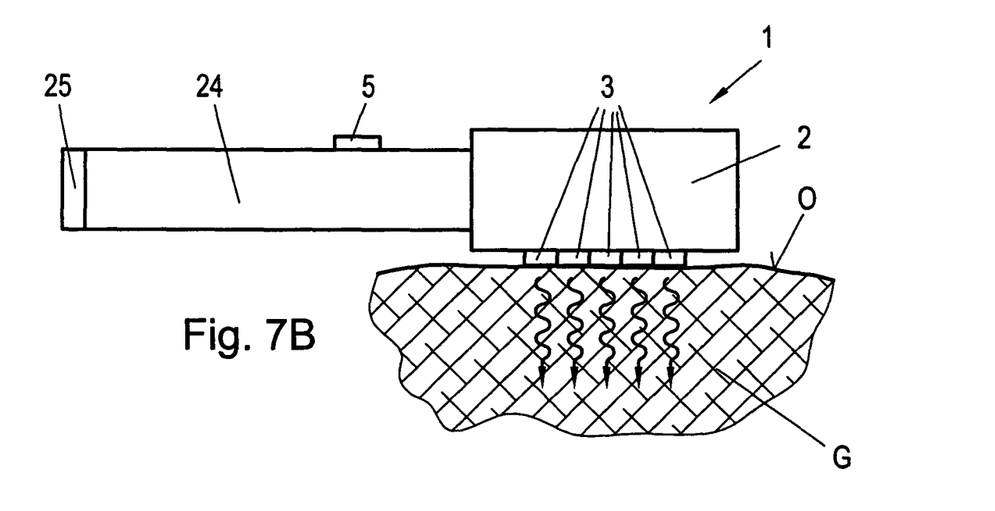

FIGS. 7A and 7B show a further embodiment of the device 1 for irradiating tissue G with light pulses L, wherein several light sources 3 are arranged on a housing 2 along a line. On the housing 2, a handle 24 may be arranged in which, e.g., the batteries for supplying the device 1 with electric energy may be arranged. Via a lid 25, the batteries can be exchanged. The device 1 is switched on and off via the activating element 5. This embodiment of the device 1 is suitable for a direct application of the light sources 3 on the surface O of the tissue G to be treated so as to attain greater penetrating depths of the light rays into the tissue G. By arranging several light sources 3 along a line, joint spaces located in deeper tissue regions can be reached and appropriately treated.

Figure 8:
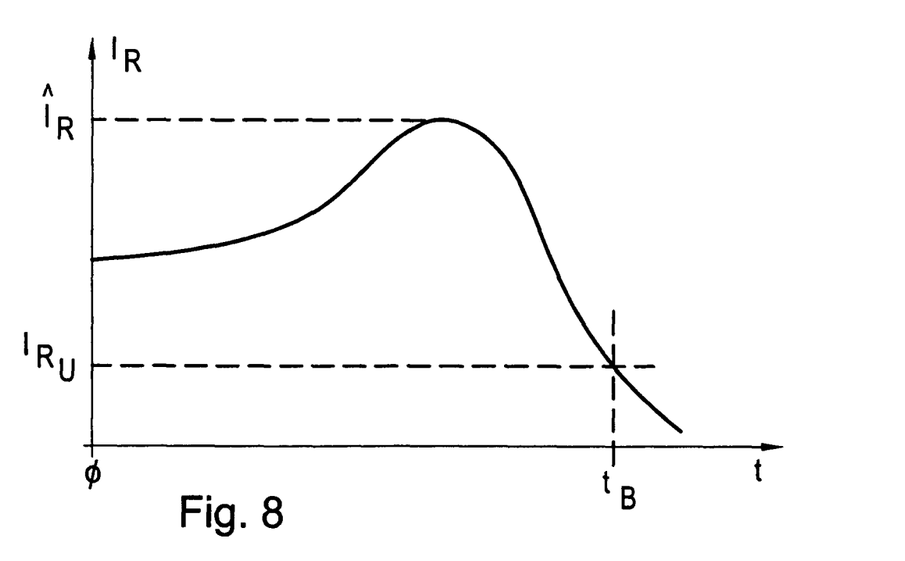
FIG. 8 shows the temporal course of the intensity of the tissue-reflected light, which temporal course is highly dependent on the type of the diseased tissue, during a treatment.

FIG. 8 shows a typical course of the intensity $I_R$ of the light reflected by the tissue G, which light increases after the onset of the treatment up to a peak value $I_R$ and subsequently drops comparatively steeply. Experience has shown that the treatment can be finished when a lower limit value $I_{R_u}$ of the intensity of the reflected light radiation has been reached. The resultant duration of treatment $t_B$ should not exceed 30 to 60 minutes so as to be acceptable to the patients.

The present device 1 for irradiating tissue G with light pulses L could be particularly successfully used in case of psoriasis and other inflammatory skin diseases. No pain was sensed during the treatment, and already after a few treatments a substantial improvement or even a cure could be achieved. Also with malignant skin diseases, such as, e.g., basaliomas, the present irradiation device 1 can be successfully employed while simultaneously using photosensitizers.

Even with metastasising and highly dangerous melanomas, there are chances for a therapy with this device 1 if a suitable sensitizer could be found.

The invention claimed is:

1. A device for irradiating tissue with light pulses, comprising a housing, at least one light source for emitting the light pulses with a single peak wavelength of from 600 nm to 660 nm, a modulator and a power stage for generating the light pulses, and with an activating element, wherein the modulator for generating the light pulses is designed with a pulse frequency of from 1 to 10 Hz, and in that the power stage for generating the light pulses is designed with a peak power density of $\geq 50$ mW/cm$^2$, based on the pulse duty factor, and in that the energy of the light pulses causes frequency doubling in the irradiated tissue, and wherein a memory for storing various values for the pulse frequency, the pulse duty factor and the power density and an operating element for selecting the desired values from the memory are provided.

2. The device of claim 1, wherein the modulator is designed for generating the light pulses with a pulse duty factor of $\leq 0.6$.

3. The device of claim 1, wherein the at least one light source is fastened to the housing such that the at least one light source can be arranged directly on the surface of the tissue to be irradiated.

4. The device of claim 3, wherein several light sources are arranged along a line.

5. The device of claim 1, wherein spacer elements are provided for producing a defined distance of the at least one light source from the surface of the tissue to be treated.

6. The device of claim 5, wherein the spacer elements are designed to be adjustable.

7. The device of claim 5, wherein a lens for bundling the light rays is arranged in front of the at least one light source or integrated therein.

8. The device of claim 5, wherein several light sources are arranged to be inclined relative to one another in ray direction.

9. The device of claim 1, wherein a sensor for detecting the light rays reflected by the surface of the irradiated tissue is provided for measuring the absorption ability of the tissue.

10. The device of claim 9, wherein the sensor is formed by an optical fiber and a photosensitive element, wherein the free end of the optical fiber is arranged at a defined distance from the surface of the tissue, and the other end of the optical fiber is connected to the photosensitive element.

11. The device of claim 10, wherein the distance of the free end of the optical fiber from the surface of the tissue is changeable.

12. The device of claim 1, wherein a reference light source and a sensor for detecting reference light radiation reflected by the tissue are provided.

13. The device of claim 12, wherein the reference light source is designed for emitting light with a wavelength of between 280 nm and 320 nm and the sensor is designed for detecting light with a wavelength of from 280 nm to 320 nm.

14. The device of claim 9, wherein the sensor is connected to an evaluation unit.

15. The device of claim 14, wherein the evaluation unit is connected to the modulator.

16. The device of claim 1, wherein the modulator is designed for generating the light pulses with a pulse frequency of 2.5 Hz and a pulse duty factor of 0.5.

17. The device of claim 1, wherein the at least one light source is formed by at least one light-emitting diode.

18. The device of claim 1, wherein batteries are provided for supplying voltage.

19. The device of claim 1, comprising a detector that detects contact of the light sources or of a spacer element with the surface of the tissue to be irradiated.

20. The device of claim 19, wherein the detector is connected to the modulator.

21. The device of claim 1, wherein a display is provided.

22. The device of claim 1, wherein the housing is designed to be splashproof.

23. The device of claim 1, wherein the light sources and the power stage are connected to a cooling element.

24. A method for irradiating tissue comprising: obtaining a device of claim 1; and using the device to irradiate tissue.

25. A method for irradiating tissue with light pulses emitted from light sources and having a single peak wave length of between 600 and 660 nm, wherein the light pulses are emitted with a pulse frequency of from 1 to 10 Hz and wherein the light pulses are emitted with a peak power density of $\geq 50$ mW/cm$^2$, based on the pulse duty factor, and the energy of the light radiation causes frequency doubling in the irradiated tissue, and wherein different values for the pulse frequency, the pulse duty factor and the power density are stored and selected before the treatment.

26. The method of claim 25, wherein the light pulses are emitted with a pulse duty factor of below 0.6.

27. The method of claim 25, wherein the light sources are arranged directly on the surface of the tissue to be treated.

28. The method of claim 25, wherein the light sources are arranged at a defined distance from the surface of the tissue to be treated.

29. The method of claim 28, wherein the light pulses are bundled.

30. The method of claim 25, wherein for measuring the absorption ability of the tissue being treated, the intensity of the light rays reflected by the surface of the tissue being treated is measured.

31. The method of claim 30, wherein the intensity of the light rays reflected by the surface of the tissue being treated are measured at a wavelength of from 280 nm to 340 nm.

32. The method of claim 25, wherein for measuring an effect of the irradiation, light rays with a wave length in the range of from 280 nm-320 nm are emitted to the tissue to be treated, and the intensity of the light rays with a wave length in the range of 280 nm-320 nm reflected by the surface of the tissue being treated is measured.

33. The method of claim 30, wherein the intensity of the light reflected from the tissue being treated is measured at a defined distance from the surface of the tissue.

34. The method of claim 30, wherein the temporal course of the intensity of the light reflected by the tissue is detected and the course of the intensity is employed for regulating the duration of treatment.

35. The method of 25, wherein the light pulses are emitted with a pulse frequency of 2.5 Hz and a pulse duty factor of 0.5.

36. The method of claim 25, wherein the energy of the light pulses is adjusted such that the duration of treatment $\leq 30$ minutes.

37. The method of claim 25, wherein a photosensitizer is used which reacts with the light pulses.

38. The method of claim 25, wherein the light sources are deactivated as soon as they are turned away from the tissue to be irradiated.

39. The method of claim 25, wherein the pulse frequency, the pulse duty factor, the power density, the energy density or the duration of treatment are displayed.

* * * * *